US008703186B2

(12) United States Patent
Mehta (10) Patent No.: US 8,703,186 B2
(45) Date of Patent: *Apr. 22, 2014

(54) ABUSE-RESISTANT ORAL DOSAGE FORMS AND METHOD OF USE THEREOF

(71) Applicant: Elite Laboratories, Inc., Northvale, NJ (US)

(72) Inventor: Atul M. Mehta, Mahwah, NJ (US)

(73) Assignee: Elite Laboratories, Inc., Northvale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/863,764

(22) Filed: Apr. 16, 2013

(65) Prior Publication Data

US 2013/0230596 A1   Sep. 5, 2013

Related U.S. Application Data (63) Continuation of application No. 12/640,344, filed on Dec. 17, 2009, now Pat. No. 8,425,933, which is a continuation of application No. 12/075,816, filed on Mar. 14, 2008, now abandoned, which is a continuation of application No. 10/409,992, filed on Apr. 8, 2003, now abandoned.

(51) Int. Cl.
*A61K 31/485* (2006.01)

(52) U.S. Cl.
USPC ............ 424/457; 424/471; 424/497; 514/282

(58) Field of Classification Search
USPC ....................................................... 424/457
See application file for complete search history.

(56) References Cited

U.S. PATENT DOCUMENTS

| | | |
|---|---|---|
| 2,770,569 A | 11/1956 | Fromherz et al. |
| 3,332,950 A | 7/1967 | Blumberg et al. |
| 3,493,657 A | 2/1970 | Lewenstein et al. |
| 3,676,557 A | 7/1972 | Lachman et al. |
| 3,773,955 A | 11/1973 | Pachter et al. |
| 3,879,555 A | 4/1975 | Pachter et al. |
| 3,965,256 A | 6/1976 | Leslie |
| 3,966,940 A | 6/1976 | Pachter et al. |
| 4,176,186 A | 11/1979 | Goldberg |
| 4,237,140 A | 12/1980 | Dudzinski |
| 4,366,310 A | 12/1982 | Leslie |
| 4,401,672 A | 8/1983 | Portoghese et al. |
| 4,443,428 A | 4/1984 | Oslack et al. |
| 4,451,470 A | 5/1984 | Ganti |
| 4,457,993 A | 7/1984 | Gordon et al. |
| 4,464,378 A | 8/1984 | Hussain et al. |
| 4,469,827 A | 9/1984 | Pusineri et al. |
| 4,573,995 A | 3/1986 | Chen et al. |
| 4,582,835 A | 4/1986 | Lewis et al. |
| 4,608,376 A | 8/1986 | Pasternak |
| 4,661,492 A | 4/1987 | Lewis et al. |
| 4,668,685 A | 5/1987 | Shami |
| 4,719,215 A | 1/1988 | Goldberg |
| 4,722,928 A | 2/1988 | Boswell et al. |
| 4,730,048 A | 3/1988 | Portoghese et al. |
| 4,760,069 A | 7/1988 | Rzeszotarski et al. |
| 4,769,372 A | 9/1988 | Kreek et al. |
| 4,774,230 A | 9/1988 | Tuttle et al. |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack et al. |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,970,075 A | 11/1990 | Oshlack |

(Continued)

FOREIGN PATENT DOCUMENTS

| | | |
|---|---|---|
| WO | WO 03/013479 | 2/2003 |
| WO | WO 03/013525 | 2/2003 |

OTHER PUBLICATIONS http://www.roehm.com/en/pharmapolymers/formulations/sustained lis . . . , "Product Overview", Feb. 16, 2005, 1 page.

Degussa, "Regulatory Information", http://www.roehm.com/en/pharmapolymers/service/regulatory.com, Feb. 16, 2005, 1 page.

Degussa, "EUDRAGIT® Versatile Polymers for Solid Oral Dosage Formulations", Rohm Pharma Polymers, Jul. 2001, 4 pages.

Paul A. Steward et al. "Studies on Permeation through Polymer Latex Films, I. Films Containing No or Only Low Levels of Additives" *Polymer International*, May 1995, 38, 1-12.

(Continued)

*Primary Examiner* — Jake Vu (74) *Attorney, Agent, or Firm* — Baker & Hostetler LLP (57) ABSTRACT

An opioid-antagonist oral dosage form which does not release a therapeutically effective amount of the opioid antagonist when the oral dosage form is orally administered to a human being, but whereby a physical alteration of the oral dosage form results in a release of the therapeutically effective amount of the opioid antagonist. An embodiment of the oral dosage form includes an opioid-antagonist layer coated onto a biologically inert pellet, and a non-releasing membrane coated onto the opioid-antagonist layer. Optionally, the oral dosage form can also include an opioid agonist, such that a method of preventing the abuse of an oral dosage form of an opioid agonist is provided by forming the oral dosage form including an opioid agonist and an opioid antagonist.

14 Claims, 1 Drawing Sheet

(56) References Cited

U.S. PATENT DOCUMENTS

| | | |
|---|---|---|
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,122,127 A | 6/1992 | Stanley |
| 5,149,538 A | 9/1992 | Granger et al. |
| 5,215,758 A | 6/1993 | Krishnamurthy |
| 5,225,440 A | 7/1993 | London et al. |
| 5,226,331 A | 7/1993 | Thompson et al. |
| 5,236,714 A | 8/1993 | Lee et al. |
| 5,256,669 A | 10/1993 | Askanazi et al. |
| 5,273,760 A | 12/1993 | Oshlack et al. |
| 5,286,493 A | 2/1994 | Oshlack et al. |
| 5,288,497 A | 2/1994 | Stanley etal. |
| 5,288,498 A | 2/1994 | Stanley |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,411,745 A | 5/1995 | Oshlack et al. |
| 5,411,965 A | 5/1995 | Reid et al. |
| 5,426,112 A | 6/1995 | Zagon et al. |
| 5,457,208 A | 10/1995 | Portoghese et al. |
| 5,460,826 A | 10/1995 | Merrill et al. |
| 5,464,841 A | 11/1995 | Portoghese et al. |
| 5,472,712 A | 12/1995 | Oshlack et al. |
| 5,472,943 A | 12/1995 | Crain et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,506,257 A | 4/1996 | MacLeod et al. |
| 5,508,042 A | 4/1996 | Oshlack et al. |
| 5,508,043 A | 4/1996 | Krishnamurthy |
| 5,512,578 A | 4/1996 | Crain et al. |
| 5,514,680 A | 5/1996 | Weber et al. |
| 5,534,492 A | 7/1996 | Aston et al. |
| 5,549,912 A | 8/1996 | Oshlack et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,601,845 A | 2/1997 | Buxton et al. |
| 5,616,601 A | 4/1997 | Khanna et al. |
| 5,622,722 A | 4/1997 | Knott et al. |
| 5,624,932 A | 4/1997 | Qin et al. |
| 5,631,263 A | 5/1997 | Portoghese et al. |
| 5,633,259 A | 5/1997 | Qin et al. |
| 5,639,476 A | 6/1997 | Oshlack et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,709,883 A | 1/1998 | Drizen et al. |
| 5,732,717 A | 3/1998 | Watanabe et al. |
| 5,763,452 A | 6/1998 | Miller et al. |
| 5,767,125 A | 6/1998 | Crain et al. |
| 5,780,479 A | 7/1998 | Kim |
| 5,785,989 A | 7/1998 | Stanley et al. |
| 5,811,126 A | 9/1998 | Krishnamurthy |
| 5,834,477 A | 11/1998 | Mioduszewski |
| 5,843,480 A | 12/1998 | Miller et al. |
| 5,846,974 A | 12/1998 | Kallman et al. |
| 5,849,240 A | 12/1998 | Miller et al. |
| 5,856,332 A | 1/1999 | Dante |
| 5,858,017 A | 1/1999 | Demopulos et al. |
| 5,860,950 A | 1/1999 | Demopulos et al. |
| 5,866,164 A | 2/1999 | Kuczynski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Muller et al. |
| 5,931,809 A | 8/1999 | Gruber et al. |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,968,824 A | 10/1999 | Spruce et al. |
| 5,972,954 A | 10/1999 | Foss |
| 5,980,882 A | 11/1999 | Eichman |
| 5,980,927 A | 11/1999 | Nelson et al. |
| 5,985,856 A | 11/1999 | Stella et al. |
| 5,998,434 A | 12/1999 | Mitch et al. |
| 6,008,258 A | 12/1999 | Inturrisi |
| 6,024,982 A | 2/2000 | Oshlack et al. |
| 6,034,091 A | 3/2000 | Dante |
| 6,068,885 A | 5/2000 | Leslie |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,143,322 A | 11/2000 | Sackler et al. |
| 6,143,328 A | 11/2000 | Heafield et al. |
| 6,153,621 A | 11/2000 | Hamann |
| 6,159,501 A | 12/2000 | Skinhoj |
| 6,162,467 A | 12/2000 | Miller et al. |
| 6,194,382 B1 | 2/2001 | Crain et al. |
| 6,203,813 B1 | 3/2001 | Gooberman |
| 6,210,714 B1 | 4/2001 | Oshlack et al. |
| 6,221,399 B1 | 4/2001 | Akehurst et al. |
| 6,228,863 B1 | 5/2001 | Palermo et al. |
| 6,254,887 B1 | 7/2001 | Miller et al. |
| 6,261,599 B1 | 7/2001 | Oshlack et al. |
| 6,264,981 B1 | 7/2001 | Zhang et al. |
| 6,277,384 B1 | 8/2001 | Kaiko et al. |
| 6,284,268 B1 | 9/2001 | Mishra et al. |
| 6,294,195 B1 | 9/2001 | Oshlack et al. |
| 6,299,901 B1 | 10/2001 | DiSanto et al. |
| 6,306,438 B1 | 10/2001 | Oshlack et al. |
| 6,310,072 B1 | 10/2001 | Smith et al. |
| 6,316,502 B1 | 11/2001 | Lai et al. |
| 6,319,954 B1 | 11/2001 | DiSanto |
| 6,326,027 B1 | 12/2001 | Miller et al. |
| 6,335,033 B2 | 1/2002 | Oshlack et al. |
| 6,342,246 B2 | 1/2002 | Johnson et al. |
| 6,362,194 B1 | 3/2002 | Crain et al. |
| 6,375,957 B1 | 4/2002 | Kaiko et al. |
| 6,387,404 B2 | 5/2002 | Oshlack et al. |
| 6,395,705 B2 | 5/2002 | Crain et al. |
| 6,399,096 B1 | 6/2002 | Miller et al. |
| 6,419,959 B1 | 7/2002 | Walter et al. |
| 6,420,433 B2 | 7/2002 | DiSanto |
| 6,436,438 B1 | 8/2002 | Momberger et al. |
| 6,458,975 B1 | 10/2002 | Bergeron, Jr. |
| 6,475,494 B2 | 11/2002 | Kaiko et al. |
| 6,476,046 B1 | 11/2002 | Wu |
| 6,491,949 B2 | 12/2002 | Faour et al. |
| 6,558,708 B1 | 5/2003 | Lin |
| 6,559,159 B2 | 5/2003 | Carroll et al. |
| 6,562,364 B2 | 5/2003 | DiSanto et al. |
| 6,569,449 B1 | 5/2003 | Stinchcomb et al. |
| 6,572,638 B1 | 6/2003 | Dae et al. |
| 6,589,991 B1 | 7/2003 | Lai et al. |
| 6,599,529 B1 | 7/2003 | Skinh et al. |
| 6,627,635 B2 | 9/2003 | Palermo et al. |

(56) References Cited

U.S. PATENT DOCUMENTS

| | | |
|---|---|---|
| 6,635,661 B2 | 10/2003 | Cuny et al. |
| 6,645,980 B1 | 11/2003 | Cuny et al. |
| 6,664,270 B2 | 12/2003 | Bergeron, Jr. |
| 6,677,332 B1 | 1/2004 | Cuny et al. |
| 6,696,066 B2 | 2/2004 | Kaiko et al. |
| 6,696,088 B2 | 2/2004 | Oshlack et al. |
| 6,713,089 B1 | 3/2004 | Bertelsen et al. |
| 6,716,449 B2 | 4/2004 | Oshlack et al. |
| 6,734,188 B1 | 5/2004 | Rhodes et al. |
| 6,753,011 B2 | 6/2004 | Faour |
| 6,762,202 B2 | 7/2004 | Marek et al. |
| 6,765,010 B2 | 7/2004 | Crain et al. |
| 6,818,656 B2 | 11/2004 | Bergeron, Jr. |
| 6,825,205 B2 | 11/2004 | Kyle |
| 6,858,580 B2 | 2/2005 | Ekwuribe et al. |
| 2001/0006967 A1 | 7/2001 | Crain et al. |
| 2001/0018069 A1 | 8/2001 | Johnson et al. |
| 2001/0041688 A1 | 11/2001 | Waeber et al. |
| 2001/0046471 A1 | 11/2001 | Marek et al. |
| 2002/0010127 A1 | 1/2002 | Oshlack et al. |
| 2002/0022048 A1 | 2/2002 | Bromberg et al. |
| 2002/0039599 A1 | 4/2002 | Lin et al. |
| 2002/0052351 A1 | 5/2002 | Hagan et al. |
| 2002/0058673 A1 | 5/2002 | Kaiko et al. |
| 2002/0065506 A1 | 5/2002 | Gruber et al. |
| 2002/0094947 A1 | 7/2002 | Crain et al. |
| 2002/0099013 A1 | 7/2002 | Piccariello et al. |
| 2002/0106329 A1 | 8/2002 | Leslie et al. |
| 2002/0119192 A1 | 8/2002 | Vishwanathan et al. |
| 2002/0132005 A1 | 9/2002 | Faour |
| 2002/0132828 A1 | 9/2002 | Carroll |
| 2002/0137761 A1 | 9/2002 | Crain et al. |
| 2002/0156056 A1 | 10/2002 | Johnson et al. |
| 2002/0156092 A1 | 10/2002 | Wu |
| 2002/0160043 A1 | 10/2002 | Coleman |
| 2002/0160991 A1 | 10/2002 | Shao |
| 2002/0173466 A1 | 11/2002 | Crain et al. |
| 2003/0003113 A1 | 1/2003 | Lewandowski |
| 2003/0004177 A1 | 1/2003 | Kao et al. |
| 2003/0022909 A1 | 1/2003 | Moss et al. |
| 2003/0026838 A1 | 2/2003 | Farrell |
| 2003/0031712 A1 | 2/2003 | Kaiko et al. |
| 2003/0044458 A1 | 3/2003 | Wright, IV et al. |
| 2003/0049317 A1 | 3/2003 | Lindsay |
| 2003/0054030 A1 | 3/2003 | Gordon |
| 2003/0055075 A1 | 3/2003 | Rubsamen |
| 2003/0059471 A1 | 3/2003 | Compton et al. |
| 2003/0064099 A1 | 4/2003 | Oshlack et al. |
| 2003/0065002 A1 | 4/2003 | Caruso et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0069418 A1 | 4/2003 | Aquila et al. |
| 2003/0073714 A1 | 4/2003 | Breder et al. |
| 2003/0082225 A1 | 5/2003 | Mason |
| 2003/0096019 A1 | 5/2003 | Currie et al. |
| 2003/0103972 A1 | 6/2003 | Pastermak et al. |
| 2003/0104976 A1 | 6/2003 | Davar et al. |
| 2003/0118641 A1 | 6/2003 | Maloney et al. |
| 2003/0124061 A1 | 7/2003 | Roberts |
| 2003/0124086 A1 | 7/2003 | Bentley et al. |
| 2003/0124185 A1 | 7/2003 | Oshlack et al. |
| 2003/0133951 A1 | 7/2003 | Coe et al. |
| 2003/0143269 A1 | 7/2003 | Oshlack |
| 2003/0144271 A1 | 7/2003 | Shulman |
| 2003/0148941 A1 | 8/2003 | Crain et al. |
| 2003/0152623 A1 | 8/2003 | Bromberg et al. |
| 2003/0153582 A1 | 8/2003 | Bergeron, Jr. |
| 2003/0157168 A1 | 8/2003 | Breder et al. |
| 2003/0166670 A1 | 9/2003 | Brooks-Korn |
| 2003/0180357 A1 | 9/2003 | Martino et al. |
| 2003/0190362 A1 | 10/2003 | Sackler et al. |
| 2003/0191147 A1 | 10/2003 | Sherman et al. |
| 2003/0194420 A1 | 10/2003 | Holl et al. |
| 2003/0203055 A1 | 10/2003 | Rao et al. |
| 2003/0209240 A1 | 11/2003 | Hale et al. |
| 2003/0211123 A1 | 11/2003 | Shukla et al. |
| 2003/0211136 A1 | 11/2003 | Kulkarni et al. |
| 2003/0211157 A1 | 11/2003 | Simon |
| 2003/0228275 A1 | 12/2003 | Ekwuribe et al. |
| 2003/0232744 A1 | 12/2003 | Crain et al. |
| 2003/0235589 A1 | 12/2003 | Demopulos et al. |
| 2003/0235595 A1 | 12/2003 | Chen et al. |
| 2003/0235617 A1 | 12/2003 | Martino et al. |
| 2004/0024003 A1 | 2/2004 | Asmussen et al. |
| 2004/0024004 A1 | 2/2004 | Sherman et al. |
| 2004/0033255 A1 | 2/2004 | Baker et al. |
| 2004/0062778 A1 | 4/2004 | Shefer et al. |
| 2004/0072864 A1 | 4/2004 | Bergeron, Jr. |
| 2004/0086561 A1 | 5/2004 | Kaiko et al. |
| 2004/0087607 A1 | 5/2004 | Crain et al. |
| 2004/0091529 A1 | 5/2004 | Edgren et al. |
| 2004/0092542 A1 | 5/2004 | Oshlack et al. |
| 2004/0109894 A1 | 6/2004 | Shefer et al. |
| 2004/0110781 A1 | 6/2004 | Harmon et al. |
| 2004/0115262 A1 | 6/2004 | Jao et al. |
| 2004/0115287 A1 | 6/2004 | Chen et al. |
| 2004/0122022 A1 | 6/2004 | Gonzales et al. |
| 2004/0126323 A1 | 7/2004 | Shevchuk et al. |
| 2004/0131552 A1 | 7/2004 | Boehm |
| 2004/0142958 A1 | 7/2004 | Herzberg et al. |
| 2004/0146547 A1 | 7/2004 | Marcenyac et al. |
| 2004/0151774 A1 | 8/2004 | Pauletti et al. |
| 2004/0156826 A1 | 8/2004 | Dangond et al. |
| 2004/0156903 A1 | 8/2004 | Abrams et al. |
| 2004/0161382 A1 | 8/2004 | Yum et al. |
| 2004/0170567 A1 | 9/2004 | Sackler |
| 2004/0176274 A1 | 9/2004 | Davar et al. |
| 2004/0176402 A1 | 9/2004 | Oshlack et al. |
| 2004/0180834 A1 | 9/2004 | Lin |
| 2004/0180916 A1 | 9/2004 | Levine |
| 2004/0186121 A1 | 9/2004 | Oshlack et al. |
| 2004/0192715 A1 | 9/2004 | Chasin et al. |
| 2004/0202717 A1 | 10/2004 | Mehta |
| 2004/0204434 A1 | 10/2004 | Shafer et al. |
| 2004/0209846 A1 | 10/2004 | Cuny et al. |
| 2004/0209850 A1 | 10/2004 | Babul |
| 2004/0213828 A1 | 10/2004 | Smith |
| 2004/0224020 A1 | 11/2004 | Schoenhard |
| 2004/0228802 A1 | 11/2004 | Chang et al. |
| 2004/0228924 A1 | 11/2004 | Oshlack et al. |
| 2004/0247646 A1 | 12/2004 | Ivory et al. |
| 2004/0247647 A1 | 12/2004 | Ivory et al. |
| 2004/0259899 A1 | 12/2004 | Sanghvi et al. |
| 2004/0266806 A1 | 12/2004 | Sanghvi et al. |
| 2005/0002997 A1 | 1/2005 | Howard et al. |
| 2005/0004155 A1 | 1/2005 | Boyd et al. |
| 2005/0008702 A1 | 1/2005 | Faour et al. |
| 2005/0014693 A1 | 1/2005 | Lin |
| 2005/0020613 A1 | 1/2005 | Boehm et al. |
| 2005/0031546 A1 | 2/2005 | Bartholomaus et al. |
| 2005/0038062 A1 | 2/2005 | Burns et al. |
| 2005/0042281 A1 | 2/2005 | Singh et al. |
| 2005/0043280 A1 | 2/2005 | Geisslinger et al. |
| 2005/0063909 A1 | 3/2005 | Wright, IV et al. |
| 2005/0074493 A1 | 4/2005 | Mehta et al. |
| 2005/0080012 A1 | 4/2005 | Mickle et al. |
| 2005/0080271 A1 | 4/2005 | Persons et al. |
| 2005/0095291 A1 | 5/2005 | Oshlack et al. |
| 2005/0106249 A1 | 5/2005 | Hwang et al. |

OTHER PUBLICATIONS

Kibbe, "Polymethacrylates" Handbook of Pharmaceutical Excipients 3rd Edition, American Pharmaceutical Association, 2000, 401-406.

ABUSE-RESISTANT ORAL DOSAGE FORMS AND METHOD OF USE THEREOF

CROSS REFERENCE TO RELATED APPLICATIONS

This application is a continuation of U.S. patent application Ser. No. 12/640,344, filed Dec. 17, 2009, now U.S. Pat. No. 8,425,933, which is a continuation of U.S. patent application Ser. No. 12/075,816 filed Mar. 14, 2008, now abandoned, which is a continuation of U.S. patent application Ser. No. 10/409,992, filed Apr. 8, 2003, now abandoned, the contents of which are herein incorporated by reference in their entireties.

TECHNICAL FIELD

The invention relates to an abuse-resistant substance, such as an opioid-antagonist, oral dosage form which does not release the opioid antagonist in a therapeutically effective amount when the oral dosage form is orally administered to a human being, but whereby a physical alteration of the oral dosage form results in a release of the opioid antagonist in an amount effective to prevent the abuse. The oral dosage form can further include an abusable substance, such as an opioid agonist, in order to prevent the abuse of the opioid agonist. A preferred embodiment of the invention includes naltrexone as the abuse-resistant substance in an oral dosage form.

BACKGROUND

Opioid agonists, or opioids, are drugs which are used primarily as analgesics. Opioid agonists act on stereospecific receptor sites in the brain, as well as in other parts of the body, which presumably regulate the feeling and perception of pain. Examples of opioid agonists include, but are not limited to, oxycodone, morphine, hydrocodone and codeine. Although they are effective in reducing the perceived pain by a patient, opioid agonists also have the characteristic of possibly being physically and psychologically addictive to the patient if used repeatedly over an extended period of time. Thus, the potential for addiction to or abuse of such drugs is an issue of concern whenever prescribing such drugs as analgesics.

For example, oxycodone is an opioid agonist which has a high potential for abuse. Oxycodone is most often administered orally, and is commercially available in a controlled-released form known as Oxycontin™ (Purdue Pharma). However, the controlled release aspect of an Oxycontin™ dosage form can be bypassed by an abuser by, for example, crushing or grinding up the dosage form, and then eating or snorting the crushed or ground-up Oxycontin™ dosage form. Thus, in this way the abuser is able to receive a relatively large single dose of the oxycodone, resulting in a euphoric "high" being experienced by the abuser.

Opioid antagonists are those drugs which serve to neutralize or block the euphoric or analgesic effect of an opioid agonist. For example, opioid antagonists are often employed to block the euphoric or analgesic effects in individuals who have overdosed on an opioid agonist, or as a daily treatment drug in individuals who are addicted to an opioid agonist. It is thought that the opioid antagonists act on and compete for the same stereospecific receptor sites in the brain as the opioid agonists, and thereby neutralize or block the resulting-analgesic or euphoric effects of the opioid agonist.

Thus, there have been previous attempts in the prior art to produce formulations and methods concerned with reducing the abuse potential of opioid agonists. For example, U.S. Pat. No. 6,228,863 to Palermo et al. describes a method of preventing the abuse of opioid dosage forms by combining an orally active opioid agonist with an opioid antagonist into an oral dosage form which would require at least a two-step extraction process to separate the opioid antagonist from the opioid agonist. According to Palermo et al., the oral dosage forms described therein had less parenteral and/or oral abuse potential than that of the prior art oral dosage forms.

In addition, U.S. Pat. No. 6,277,384 to Kaiko et al. describes oral dosage forms including combinations of opioid agonists and opioid antagonists in ratios which are analgesically effective when administered orally, but which are aversive in a physically dependent individual. According to Kaiko et al., the oral dosage forms described therein had less oral abuse potential than that of the prior art oral dosage forms.

Furthermore, U.S. Pat. No. 5,236,714 to Lee et al. is directed to an abusable substance dosage form having a reduced abuse potential. Lee et al. disclose compositions and dosage forms for administering abusable substances wherein the therapeutic effect of the abusable substance will not be diminished, although the abuse potential of the abusable substance will be diminished. Specifically, topical compositions for application to a patient's skin or mucosa are disclosed including an abusable substance present in a form which is permeable to the skin or mucosa to which the composition is to be applied, and an antagonist present in a form which is impermeable to the skin or mucosa to which the composition is to be applied, such that if an attempt were made to abuse the composition by administering it through another bodily portal, the antagonist would prevent the occurrence of the abusive effect by producing its antagonistic effect. In addition, Lee et al. disclose dosage forms comprising a drug reservoir composition including an abusable substance and at least one antagonist enclosed within an abusable substance releasing means, wherein the abusable substance is present in a form which is permeable through the releasing means and the antagonist is present in a form which is impermeable to the releasing means. As with the topical composition, Lee et al. disclose that if an attempt were made to abuse the drug reservoir composition by removing it from the dosage form and administering it through another bodily portal, the antagonist would prevent the occurrence of the abusive effect by producing its antagonistic effect. The dosage forms of Lee et al. include a single abusable substance releasing means which controls the release of both the abusable substance and the antagonist.

However, there is still a need in the art for an improved oral dosage form of an opioid antagonist which would reduce the abuse potential of an opioid agonist.

SUMMARY

An embodiment of the present invention is directed to an opioid-antagonist oral dosage form wherein the opioid antagonist does not release unless the oral dosage form is crushed or ground up, thereby antagonizing the opioid effect of an opioid agonist.

An embodiment of the oral dosage form of the present invention comprises: a biologically inert pellet; an opioid-antagonist layer coated on the biologically inert pellet, wherein the opioid-antagonist layer comprises a therapeutically effective amount of an opioid antagonist; and a non-releasing membrane coated on the opioid antagonist layer, wherein the non-releasing membrane comprises a water-retardant polymer and may contain a lubricant; wherein the oral dosage form does not release the therapeutically effective amount of the opioid antagonist when the oral dosage form is orally administered to a human being, and wherein a physical alteration of the oral dosage form results in a release of the therapeutically effective amount of the opioid antagonist.

In another embodiment of the invention, the oral dosage form can also include a second pellet comprising an opioid agonist, and/or other pain relievers and anti-inflammatory agents.

In a further embodiment of the invention, the oral dosage form comprises: an opioid-antagonist formulation, wherein the opioid-antagonist formulation comprises a therapeutically effective amount of an opioid antagonist; and a non-releasing membrane coated on the opioid-antagonist formulation, wherein the non-releasing membrane comprises a water-retardant polymer and may contain a lubricant; wherein the oral dosage form does not release the therapeutically effective amount of the opioid antagonist when the oral dosage form is orally administered to a human being, and wherein a physical alteration of the oral dosage form results in a release of the therapeutically effective amount of the opioid antagonist.

The invention is also directed to a method of preventing the abuse of an oral dosage form of an opioid agonist. An embodiment of the method of the invention includes the forming of an oral dosage form by combining: (1) a first type of pellet comprising an opioid agonist; and (2) a second type of pellet comprising: a biologically inert pellet; an opioid-antagonist layer coated on the biologically inert pellet, wherein the opioid-antagonist layer comprises a therapeutically effective amount of an opioid antagonist; and a non-releasing membrane coated on the opioid antagonist layer, wherein the non-releasing membrane comprises a water-retardant polymer. The oral dosage form does not release the therapeutically effective amount of the opioid antagonist when the oral dosage form is orally administered to a human being, and a physical alteration of the oral dosage form results in a release of the therapeutically effective amount of the opioid antagonist.

Another embodiment of the method of the invention includes coating a non-releasing membrane onto an opioid-antagonist formulation, and coating an opioid-agonist layer onto the non-releasing membrane to form an oral dosage form, wherein the opioid-antagonist formulation comprises a therapeutically effective amount of an opioid antagonist, the non-releasing membrane comprises a water-retardant polymer, and the opioid-agonist layer comprises an opioid agonist. The oral dosage form does not release the therapeutically effective amount of the opioid antagonist when the oral dosage form is orally administered to a human being, and a physical alteration of the oral dosage form results in a release of the therapeutically effective amount of the opioid antagonist.

In addition, a further embodiment of the method of the invention also includes adding other pain relievers and/or anti-inflammatory agents when forming the oral dosage form.

DETAILED DESCRIPTION OF ILLUSTRATIVE EMBODIMENTS

The present invention, as disclosed and described herein, provides a novel oral dosage form of a therapeutically effective amount of an opioid antagonist which does not release when orally administered to a human being, but which does release upon a physical alteration of the oral dosage form. That is, if the oral dosage form of the invention is orally administered to a human being, then the therapeutically effective amount of the opioid antagonist is not released from the oral dosage form, and thus an opioid agonist will have its intended analgesic effect on the human being. As used herein, the phrase "a therapeutically effective amount of an opioid antagonist" refers to that amount of the opioid antagonist which is sufficient to antagonize the opioid agonist and thus effectively neutralize the intended analgesic effect of the opioid agonist. Thus, when orally administered to a human being, although the oral dosage form of the invention may release a negligible or inconsequential amount of the opioid antagonist, it will not release an amount to antagonize the opioid agonist and to neutralize its intended analgesic effect.

However, if the oral dosage form of the invention is physically altered in any way, such as by crushing or grinding of the oral dosage form, then the therapeutically effective amount of the opioid antagonist will be released. That is, as the non-releasing membrane of the oral dosage form is rendered ineffective by physical alteration, the opioid antagonist will no longer be effectively coated by the non-releasing membrane and the therapeutically effective amount of the opioid antagonist will thereby be released. Therefore, the opioid agonist will be antagonized by the opioid antagonist and the intended analgesic effect of the opioid agonist will be effectively neutralized, reduced or blocked. Thus, if an individual were to crush and grind up the oral dosage form of the present invention in an attempt to take it parenterally, or orally, or by snorting it through the nose, in order to obtain a euphoric "high," a sufficient amount of the opioid antagonist would thereby be released to antagonize the opioid agonist and to neutralize or block its intended euphoric, analgesic effect.

Depending upon the specific opioid antagonist(s) present in the embodiment of the oral dosage form of the present invention, the dose of the opioid antagonist(s) will vary. For example, a single 50 mg dose of naltrexone is generally sufficient to block the analgesic effect of an opioid agonist. See, e.g., U.S. Pat. Nos. 6,228,863 and 6,277,384. The dosage amount of any of the opioid antagonists which can be used in accordance with the invention can readily be determined by one of ordinary skill in the art. As mentioned above, the dosage amount of the opioid antagonist will be at least that amount of the opioid antagonist which is sufficient to antagonize the opioid agonist and thus effectively neutralize the intended analgesic effect of the opioid agonist.

The invention provides an oral dosage form which does not release a therapeutically effective amount of an opioid antagonist when the oral dosage form is orally administered to a human being. That is, the oral dosage form of the invention is designed such that when orally administered to a human being, it would not provide effective blood levels of the opioid antagonist for up to about twenty-four (24) hours and beyond, at which time the opioid agonist would have previously been released and would have had its intended analgesic effect on the human being.

According to an embodiment of the invention, the oral dosage form includes a biologically inert pellet (core) coated first by an opioid-antagonist layer, which is then coated by a non-releasing membrane. Many types of inert pellets are suitable for use in forming the core of this embodiment of the oral dosage form, and are commercially available from a number of companies; for example, non-pareils, sugar and/or starch-based pellets are all suitable types of pellets. Sugar spheres of particle size 25 to 30 mesh are particularly preferred, although any inert pellets of mesh size within the range of 14 mesh to 60 mesh are also preferred for use in this invention. In addition, other substrates, including but not limited to, granules, spheroids and beads, may be used in accordance with this embodiment of the invention.

In this embodiment of the invention, an opioid-antagonist layer coats the biologically inert pellet of the oral dosage form. The opioid-antagonist layer comprises a therapeutically effective amount of an opioid antagonist. Any opioid antagonist, or a pharmaceutically acceptable salt thereof, or combinations thereof, may be used in accordance with the invention. Examples of a suitable opioid antagonist, include but are not limited to, naltrexone, naloxone, and nalmephene. Preferably, the opioid antagonist comprises naltrexone.

The opioid-antagonist layer may also include a binder agent to enhance its adherence to the biologically inert pellet. Suitable binder agents for use in the opioid-antagonist layer of the invention include, but are not limited to, hydroxypropylmethyl cellulose (HPMC) (3 to 6 cps, preferably 6 cps), hydroxyethyl cellulose, hydroxypropyl cellulose, methyl cellulose, polyvinyl pyrrolidone and the like. Preferably, hydroxypropylmethyl cellulose, and most preferably, hydroxypropylmethyl cellulose E6 or Opadry®clear is used in accordance with the invention. Preferably, the binder agent is dissolved in water (or any suitable solvent) to form a 5% to 30% (w/w) solution, preferably a 7% to 25% (w/w) solution and most preferably, an approximately 10% (w/w) solution. The solution of binder agent is admixed with a solution or suspension of the opioid antagonist, and then applied onto the biologically inert pellets by conventional spray techniques. For example, the opioid antagonists/binder agent solution or suspension may be applied to the biologically inert pellets by spraying the solution or suspension onto the pellets using a fluid bed processor. Preferably, the amount of binder agent included in the opioid-antagonist layer is in a ratio of binder agent to opioid-antagonist of about 1:10, although any ratio is suitable for use with the present invention.

The opioid-antagonist layer of this embodiment of the oral dosage form of the present invention may also include one or more pharmaceutically acceptable excipients in addition to the opioid antagonist and the optional binder agent. Suitable pharmaceutically acceptable excipients which may be employed in the invention are well known to those of ordinary skill in the art and include any conventional pharmaceutically acceptable excipient, such as an antifoam agent, which is added to aid the formulation process. The opioid-antagonist layer may also include a suitable carrier, diluent, surfactant and/or lubricant.

In another embodiment of the invention, the opioid-antagonist layer is coated with an optional sealing layer. The sealing layer contains a water soluble polymer, which may be the same or different from the binder agent present in the opioid-antagonist layer. For example, the sealing layer may include a water soluble polymer such as hydroxypropylmethyl cellulose (3 to 6 cps, preferably 6 cps), hydroxyethyl cellulose, hydroxypropyl cellulose, methyl cellulose, polyvinylpyrrolidone and the like. Preferably, hydroxypropylmethyl cellulose, and most preferably, hydroxypropylmethyl cellulose-E-6 is employed in the sealing layer. In addition, the sealing layer may optionally contain a lubricant, such as for example, calcium stearate, magnesium stearate, zinc stearate, stearic acid, talc or a combination thereof The total amount of this optional sealing layer contained in the finally coated pellets is preferably about 0.5% to about 5% of the total weight of the finally coated pellet.

In a further embodiment of the invention, the oral dosage form includes an opioid-antagonist formulation comprising a therapeutically effective amount of an opioid antagonist, which is then coated by a non-releasing membrane. In this embodiment of the invention, the opioid-antagonist formulation may be produced by any method known in the art, including but not limited to, forming a matrix system of the opioid antagonist which would then be compressed into a tablet. Furthermore, the opioid-antagonist formulation may be provided in any form known in the art, including but not limited to, pellets, granules, spheroids, capsules and tablets. As would be understood by one of ordinary skill in the art, such an opioid-antagonist formulation could further include, for example, binder agents, diluents, carriers, fillers, lubricants and other pharmaceutically acceptable additives and excipients which are used in the formation of the particular form of the formulation, and all such opioid-antagonist formulations are within the scope of the present invention. In further embodiments of the invention, the opioid-antagonist formulation may be coated with an optional sealing layer prior to coating with the non-releasing membrane.

According to the present invention, the oral dosage form also includes a non-releasing membrane which is coated onto the opioid-antagonist layer, the opioid-antagonist formulation, or the optional sealing layer, depending upon the particular embodiment of the oral dosage form. The non-releasing membrane serves to protect the integrity of the biologically inert pellets coated with the opioid-antagonist layer, or the opioid-antagonist formulation, such that the therapeutically effective amount of the opioid antagonist is not released from the oral dosage form when it is orally administered to a human being. At the same time however, if the oral dosage form is physically altered and the non-releasing membrane is rendered ineffective, then the therapeutically effective amount of the opioid antagonist is thereby released from the oral dosage form.

The non-releasing membrane of the invention comprises a water-retardant polymer, such as, for example, an alkyl cellulose, an acrylic acid polymer, an acrylic acid copolymer, a methacrylic acid polymer, a methacrylic acid copolymer, shellac, zein, or hydrogenated vegetable oil. The water-retardant polymer is physiologically acceptable, and it substantially prevents the release of the opioid antagonist. In addition, the water-retardant polymer could optionally be water insoluble. A preferred water-retardant polymer is a poly (meth)acrylate polymer, such as Eudragit NE 30 D or Eudragit NE 40 D, or a combination thereof Most preferably, the water-retardant polymer comprises the poly(meth)acrylate polymer, Eudragit NE 30 D. Eudragit NE 30 D and Eudragit NE 40 D polymers are available from Rhom Pharma, D-6108 Weiterstadt 1, Dr. Otto-Rohm-Str. 2-4, Germany. Eudragit NE 30 D and Eudragit NE 40 D are pH independent polymers available as 30% or 40% aqueous dispersions, respectively. Furthermore, Eudragit RS 30 D, Eudragit RL 30 D, Eudragit S and Eudragit L 30 D are further examples of suitable water-retardant polymers. When employing Eudragit NE 30 D as the water-retardant polymer, the NE30D solids in the non-releasing membrane generally constitute about 15% to about 80% of the total weight of the solids content of the final oral dosage form, preferably about 25% to about 60%, and most preferably about 30% to about 50% of the total weight of the solids content of the final oral dosage form.

In a preferred embodiment of the present invention, the non-releasing membrane contains in addition to a water-retardant polymer, an amount of a lubricant, such as for example, calcium stearate, magnesium stearate, zinc stearate, stearic acid, talc or a combination thereof, to form the non-releasing membrane. In particular, it is preferred that the non-releasing membrane contains an amount of magnesium stearate, or other lubricant, sufficient to provide non-release of the opioid antagonist for up to about 14-24 hours after administration of the dosage form to a human being. In a most preferred embodiment, the non-releasing membrane contains magnesium stearate admixed with the water-retardant polymer, which is preferably Eudragit NE30D. In embodiments of the invention including opioid-antagonist-coated pellets, the lubricant functions to prevent agglomeration of the opioid-antagonist-coated pellets during processing and also helps to prevent release of the opioid antagonist from the opioid-antagonist-coated pellets. Preferably, the final, dried non-releasing membrane contains about 5% to about 50% magnesium stearate and/or other lubricant(s), and more preferably about 7% to about 30%, and most preferably about 10% to about 25% lubricant(s) based on the total weight of solids content of the total formulation.

In another embodiment of the invention, the non-releasing membrane is coated with an optional sealing layer. This optional sealing layer is similar to the previously described optional sealing layer between, for example, the opioid-antagonist layer and the non-releasing membrane, and in fact may be comprised of the same exact elements. Thus, the sealing layer contains a water soluble polymer, which may be the same or different from the binder agent present in the opioid-antagonist layer. For example, the sealing layer may include a water soluble polymer such as hydroxypropylmethyl cellulose (3 to 6 cps, preferably 6 cps), hydroxyethyl cellulose, hydroxypropyl cellulose, methyl cellulose, polyvinylpyrrolidone and the like. Preferably, hydroxypropylmethyl cellulose, and most preferably, hydroxypropylmethyl cellulose-E-6 is employed in the sealing layer. In addition, the sealing layer may optionally contain a lubricant, such as for example, calcium stearate, magnesium stearate, zinc stearate, stearic acid, talc or a combination thereof. In embodiments of the invention employing pellets, the total amount of this optional sealing layer contained in the finally coated pellets is preferably about 0.5% to about 10% of the total weight of the finally coated pellet. In further embodiments of the invention, the optional sealing layer may also be coated with an enteric layer.

In a further embodiment of the invention, the non-releasing membrane is coated with an enteric layer comprising an enteric coating polymer, and optionally comprising a plasticizer. A preferred enteric coating polymer is Eudragit L 30D. Suitable plasticizers for inclusion in the enteric layer include, for example, triethyl citrate, polyethylene glycol, dibutyl phthalate, diethylphthalate and triacetin. In embodiments of the invention employing pellets, the optional enteric layer, which is pH dependant and resistant to gastric fluids, preferably comprises from about 0.5% to about 10% of the total weight of the finally coated pellet. In further embodiments of the invention, the enteric layer may also be coated with a sealing layer.

In another embodiment of the invention, the non-releasing membrane (optionally coated with an enteric layer and/or a sealing layer) is coated with an opioid-agonist layer comprising an opioid agonist. Any opioid agonist, or a pharmaceutically acceptable salt thereof, may be used in accordance with the invention. Examples of the opioid agonist which may be included in this embodiment of the invention include, but are not limited to, oxycodone, hydrocodone, morphine, hydromorphone, codeine, and mixtures thereof. Preferably, the opioid agonist comprises oxycodone. In further embodiments of the invention, the opioid-agonist layer may also be coated with a sealing layer and/or an enteric layer.

In the present invention, the opioid agonist is preferably present in an amount which will provide for effective blood levels of the opioid agonist in a human being. That is, when the oral dosage form of the invention is orally administered to a human being, the opioid agonist will be released from the oral dosage form, and it can thus have its intended analgesic effect upon the human being. This is because, as described above, upon oral administration of the oral dosage form of the invention, the opioid antagonist will not be sufficiently released from the oral dosage form, thereby enabling the opioid agonist to have its intended analgesic effect. At the same time, however, if the oral dosage form of the invention is physically altered in any way, such as by grinding or crushing, then the therapeutically effective amount of the opioid antagonist will be released from the oral dosage form, thereby antagonizing the opioid agonist and thus effectively neutralizing the intended analgesic effect of the opioid agonist. Thus, the formation of the oral dosage form of the invention is an effective method of preventing the abuse of an oral dosage form of an opioid agonist. For example, if an individual were to crush and grind up the oral dosage form of the present invention in an attempt to take it parenterally, orally, or by snorting it through the nose, in order to obtain a euphoric "high", a sufficient amount of the opioid antagonist would thereby be released to antagonize the opioid agonist and to neutralize or block its intended euphoric, analgesic effect.

In addition, the opioid-agonist layer of this embodiment may further include, for example, binder agents, diluents, carriers, fillers, lubricants and other pharmaceutically acceptable additives and excipients which may or may not effect the rate of release of the opioid agonist from the oral dosage form of this embodiment. Thus, any type of release profile known in the art, including but not limited to, immediate and sustained release formulations, may be used in accordance with the opioid-agonist layer of this embodiment.

The opioid-antagonist layer, the opioid-antagonist formulation, and/or the non-releasing membrane of the invention may each further comprise diluents, carriers, fillers and other pharmaceutical additives which may or may not effect the rate of release of the opioid antagonist from the oral dosage form of the invention. For example, the non-releasing membrane preferably contains a lubricant and the opioid-antagonist layer may optionally contain a surfactant. The opioid-antagonist layer, the opioid-antagonist formulation, and/or the non-releasing membrane may also further contain pharmaceutically acceptable excipients such as anti-adherents, and pharmaceutically acceptable pigments such as titanium dioxide, iron oxide and various color pigments including vegetable dyes, and the like.

In embodiments of the invention employing pellets, the opioid-antagonist loaded pellets preferably provide in total a potency of about 6% to about 70% (w/w) based upon the total weight of the layered pellets, although the potency can be adjusted as desired. For example, when the opioid antagonist employed in the invention is naltrexone, it is preferred that the layered pellets be formulated at about 60% potency (w/w). However, the skilled practitioner can formulate the oral dosage forms of the invention to have any desired total potency of opioid antagonist.

The non-release, oral dosage form of the invention, as disclosed herein, is designed such that it does not provide for effective blood levels of the opioid antagonist for at least 24 hours after oral administration of the oral dosage form. In addition, the non-release, oral dosage form provides a dissolution rate of the opioid antagonist, when measured in vitro by the U.S. Pharmacopeia XXVI basket method of 100 rpm in 900 ml of water at 37° C., wherein the therapeutically effective amount of the opioid antagonist is not released from the dosage form after about 14 to 24 hours.

The process for making an embodiment of the oral dosage form of the invention includes coating at least one layer of an opioid antagonist onto the surface of a biologically inert pellet (e.g., a non-pareil pellet (sugar and/or starch-based pellets)) to form opioid-antagonist loaded pellets. The opioid-antagonist loaded pellets are then coated with a non-releasing membrane.

In preparing an embodiment of the oral dosage form of the invention, the opioid-antagonist layer may be applied by spraying the opioid-antagonist suspension onto sugar spheres or other biologically inert pellets that have been suspended in a fluidized bed, for example. Other conventional spray techniques such as pan coating may also be used. The opioid-antagonist loaded pellets can also be prepared by an extruder/marumerizer. After the sugar spheres or pellets are coated with the opioid-antagonist layer, they may optionally be dried by air exposure, or other methods known in the art (although drying may occur spontaneously from air flow in the fluid bed processor).

In this embodiment, the non-releasing membrane including the water-retardant polymer is next coated onto the opioid-antagonist loaded pellets. The water-retardant polymer comprising the non-releasing membrane is generally prepared as a dispersion and sprayed onto the opioid-antagonist loaded pellets. The total amount of water-retardant polymer in the pellets is in the range of from about 15% to about 80% of the total weight of the prepared pellets, preferably about 30% to about 55% of the total weight of the prepared pellets. By varying the amount of water-retardant polymer within this range, the desired non-release of the opioid antagonist is achieved.

At the final stage in preparing this embodiment, the coated pellets may optionally be subjected to a curing process. For example, the coated pellets may be cured at a temperature in the range of from about 30° to about 50° C., preferably from about 35° to about 45° C., and most preferably about 40° C., for a period of about 5 to about 10 days and, preferably, about 7 days. A further example of a suitable curing process could be performed in a fluid bed processor for about 1 to about 5 hours at about 40° to about 80° C., preferably for about 3 hours at about 55° to about 65° C., and most preferably for about 1 hour at about 60° C.

The coated pellets may then be weighed out according to the total dose of opioid antagonist to be administered to patients. Diluent may be added, such as, for example, dextrose, sorbitol, mannitol, microcrystalline cellulose, methocel ether, lactose, glyceryl palmitostearate, glyceryl stearate, glyceryl behenate, and combinations thereof, among other commonly used pharmaceutical diluents, and the mixture of coated pellets and diluents pressed into tablets. Alternatively, the coated pellets, with or without diluents, can be encapsulated in a capsule, such as a hard gelatin capsule. Furthermore, in an embodiment of the invention, the opioid agonist(s) can also be added to a tablet or capsule containing the opioid-antagonist loaded pellets.

It is often desirable to add inert diluent when formulating the coated pellets into tablet form. The presence of pharmaceutical diluents, such as microcrystalline cellulose, methocel ether, glyceryl palmitostearate, glyceryl stearate, and/or glyceryl behemate, for example, in the coated pellet mixture serves to cushion the pellets so that they are not significantly ruptured during compression. In addition, pharmaceutical diluents can be added to enhance the non-releasing property of the oral dosage form of the present invention.

In general, the release rate of opioid antagonist from the coated pellets is dependent upon a number of factors including, inter alia, the overall structure and design of the coated pellet, the potency of the coated pellet, the type and amount of water-retardant polymer present in the non-releasing membrane, and when present in the coated pellets, the type and amount of lubricant. The coated pellets may be formulated into tablets or encapsulated in the desired dosage amount. Typical unit dosage amounts for the opioid antagonist of the oral dosage form of the invention include any dosage between about 1 and 200 mg, although dosages outside of this range may also be employed in the present invention.

In another embodiment of the oral dosage form of the invention, in addition to the coated pellets described above which are coated with an opioid antagonist, the oral dosage form may include an opioid-agonist formulation including an opioid agonist. The opioid-agonist formulation may be produced by any method known in the art, including the method described above wherein pellets are coated by use of a fluid bed processor. In addition, the opioid-agonist formulation may be provided in any form known in the art, including but not limited to, pellets, granules, spheroids, capsules and tablets, with any type of release profile, including but not limited to, immediate and sustained release formulations. Any opioid agonist, combinations thereof, or a pharmaceutically acceptable salt thereof, may be used in accordance with the invention. Examples of the opioid agonist which may be included in the oral dosage form of the invention include, but are not limited to, oxycodone, hydrocodone, morphine, hydromorphone, codeine, and mixtures thereof. Preferably, the opioid agonist comprises oxycodone.

In this embodiment of the invention, the opioid agonist is preferably present in an amount which will provide for effective blood levels of the opioid agonist in a human being. That is, when this embodiment of the oral dosage form of the invention is orally administered to a human being, the opioid agonist will be released from the oral dosage form, and it can thus have its intended analgesic effect upon the human being. This is because, as described above, upon oral administration of the oral dosage form of the invention, the opioid antagonist will not be sufficiently released from the oral dosage form, thereby enabling the opioid agonist to have its intended analgesic effect. At the same time, however, if this embodiment of the oral dosage form of the invention is physically altered in any way, such as by grinding or crushing, then the therapeutically effective amount of the opioid antagonist will be released from the oral dosage form, thereby antagonizing the opioid agonist and thus effectively neutralizing the intended analgesic effect of the opioid agonist. Thus, the formation of the oral dosage form of this embodiment is an effective method of preventing the abuse of an oral dosage form of an opioid agonist. For example, if an individual were to crush and grind up the oral dosage form of the present invention in an attempt to take it parenterally, orally, or by snorting it through the nose, in order to obtain a euphoric "high", a sufficient amount of the opioid antagonist would thereby be released to antagonize the opioid agonist and to neutralize or block its intended euphoric, analgesic effect.

The following examples are illustrative of the invention, and are not to be construed as limiting the invention in any way.

EXAMPLES

In these examples, embodiments of the oral dosage form of the invention were prepared as follows.

Step 1: Applying an Opioid Antagonist Layer to a Biologically Inert Pellet

Ingredients

|  | Example 1 | Example 2 |
|---|---|---|
| naltrexone hydrochloride | 50 grams | 531 grams |
| hydroxypropylmethyl cellulose (HPMC) (methocel E6 10% solution) (i.e., 90% water) | 50 grams | 530 grams |
| purified water | 175 grams | 1050 grams |
| simethicone 30% emulsion (i.e., 70% water) | 1 gram | 10 grams |
| 25/30 mesh sugar spheres | 750 grams | 413 grams |
| total weight: | 805.3 grams | 1000 grams |

Note:
the water is evaporated during this process and is thus not part of the total weight.

Method

An opioid-antagonist suspension was prepared by mixing the methocel E6 10% solution (binder agent), the naltrexone hydrochloride (opioid antagonist), the simethicone 30% emulsion (antifoam agent) and the purified water (in the amounts listed above for each example). This opioid-antagonist suspension was then sprayed onto the 25/30 mesh sugar spheres using a fluid bed processor, resulting in biologically inert pellets coated with an opioid-antagonist layer. In Example 1, these coated pellets have a naltrexone (opioid antagonist) potency of 6.2%, and in Example 2, these coated pellets have a naltrexone (opioid antagonist) potency of 53%.

Step 2: Applying a Non-Releasing Membrane to the Coated Pellets of Example 1 from Step 1

Ingredients

| coated pellets of Example 1 from step 1 | 650 grams |
|---|---|
| Eudragit NE 30 D 30% dispersion | 700 grams |
| magnesium stearate 15% suspension | 560 grams |

Method

Next, the Eudragit NE 30D 30% dispersion and the magnesium stearate 15% suspension (in the amounts listed above) were added together and mixed to form a non-releasing suspension. This non-releasing suspension was then sprayed onto 650 grams of the coated pellets of Example 1 from step 1 using a fluid bed processor. These twice-coated pellets were then cured in the fluid bed processor for about 6 hours at 60° C.

Step 3: Filling into Capsules

The coated pellets from step 2 were then filled into capsules to give an effective dose of 50 mg naltrexone hydrochloride.

Step 4: In-Vitro Dissolution Testing

Figure 1:
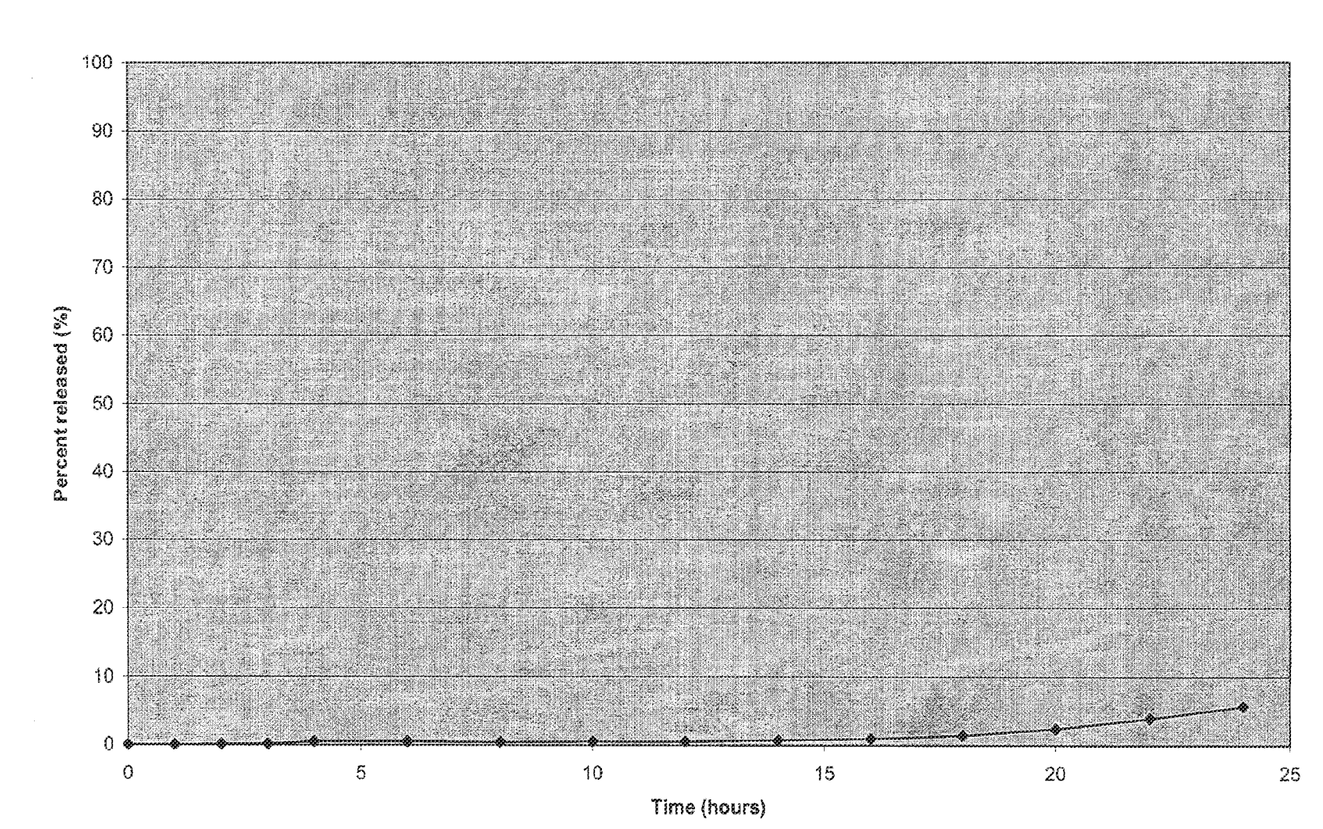
FIG. 1 shows a graph of the in vitro release of naltrexone hydrochloride from an embodiment of the oral dosage form of the present invention.

Dissolution testing was then performed on the capsules prepared in step 3 as described above. In this example, the Eudragit NE 30D solids coating constituted 42.48% of the final formulation (i.e., the capsule), and the total solids coating constituted 59% of the final formulation (i.e., the capsule). As used herein, the "total solids coating" refers to the Eudragit NE 30D and the magnesium stearate, as described above in step 2. The conditions for testing were those of the USP Basket Method of 100 rpm in 900 ml of de-ionized water at 37° C., with the results shown below in Table 1. A graph of these in vitro dissolution testing results can be seen in FIG. 1.

TABLE 1

Dissolution Data

| Time (in hours) | Percentage of Naltrexone Released |
|---|---|
| 0 | 0 |
| 1 | 0 |
| 2 | 0.1 |
| 3 | 0.1 |
| 4 | 0.5 |
| 6 | 0.5 |
| 8 | 0.4 |
| 10 | 0.5 |
| 12 | 0.5 |
| 14 | 0.7 |
| 16 | 0.9 |
| 18 | 1.4 |
| 20 | 2.4 |
| 22 | 3.9 |
| 24 | 5.7 |

As can be seen from Table 1 above, in this embodiment of the oral dosage form of the invention, the therapeutically effective amount of the naltrexone is still not released from the dosage form after about 14 to 24 hours, as only 5.7% of the naltrexone has been released from the dosage form after about 24 hours. Thus, in this example, 5.7% of the 50 mg naltrexone (i.e., about 2.85 mg) has been released after about 24 hours, which is insufficient to block or neutralize the intended analgesic effect of an opioid agonist.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed:

1. A pellet comprising:
   a biologically inert pellet;
   an opioid-antagonist layer coated on the biologically inert pellet, wherein the opioid-antagonist layer comprises a therapeutically effective amount of an opioid antagonist; and
   a non-releasing membrane coated on the opioid-antagonist layer, wherein the non-releasing membrane comprises a water-retardant polymer that is a EUDRAGIT® NE 30D or NE 40D non-ionic poly(ethyl acrylate-co-methyl methacrylate), wherein the at least one water-retardant polymer constitutes about 42% to about 50% by weight of the solids content of the pellet.

2. The pellet of claim 1, wherein the non-releasing membrane further comprises a lubricant.

3. The pellet of claim 2, wherein the lubricant comprises calcium stearate, magnesium stearate, zinc stearate, stearic acid, talc or a combination thereof.

4. The pellet of claim 1, wherein the opioid-antagonist layer further comprises a binder agent.

5. The pellet of claim 4, wherein the binder agent comprises a hydroxypropylmethyl cellulose, hydroxyethyl cellulose, hydroxypropyl cellulose, methyl cellulose or polyvinyl pyrrolidone.

6. The pellet of claim 1, wherein the opioid-antagonist layer further comprises a sealing layer between the opioid-antagonist layer and the non-releasing membrane.

7. The pellet of claim 1, wherein the opioid-antagonist layer further comprises at least one of an enteric layer and a sealing layer coated on the non-releasing membrane.

8. The pellet of claim 1, wherein the opioid-antagonist is naltrexone, naloxone, or nalmephene.

9. The pellet of claim 1, wherein the opioid-antagonist is naltrexone.

10. The pellet of claim 1, further comprising an opioid-agonist layer comprising an opioid agonist.

11. The pellet of claim 10, wherein the opioid agonist is oxycodone, hydrocodone, morphine, hydromorphone, codeine, or mixtures thereof.

12. The pellet of claim 10, wherein the opioid agonist is oxycodone.

13. The pellet of claim 10, wherein the opioid agonist is morphine.

14. A method comprising providing to a patient at least one pellet of claim 10.

\* \* \* \* \*